(12) United States Patent
Kim

(10) Patent No.: US 10,476,450 B2
(45) Date of Patent: Nov. 12, 2019

(54) RECONFIGURABLE AMPLIFIER AND AMPLIFICATION METHOD THEREOF

(71) Applicant: SAMSUNG ELECTRONICS CO., LTD., Suwon-si (KR)

(72) Inventor: JongPal Kim, Seoul (KR)

(73) Assignee: Samsung Electronics Co., Ltd., Suwon-si (KR)

(*) Notice: Subject to any disclaimer, the term of this patent is extended or adjusted under 35 U.S.C. 154(b) by 0 days.

(21) Appl. No.: 15/917,895

(22) Filed: Mar. 12, 2018

(65) Prior Publication Data

US 2019/0036497 A1  Jan. 31, 2019

(30) Foreign Application Priority Data

Jul. 31, 2017 (KR) .................. 10-2017-0097090

(51) Int. Cl.
*H03F 3/04* (2006.01)
*A61B 5/0428* (2006.01)
(Continued)

(52) U.S. Cl.
CPC .............. *H03F 3/04* (2013.01); *A61B 5/0428* (2013.01); *A61B 5/04284* (2013.01);
(Continued)

(58) Field of Classification Search
CPC ........................................................ H03F 3/04
See application file for complete search history.

(56) References Cited

U.S. PATENT DOCUMENTS 5,847,600 A * 12/1998 Brooks .................... H03F 3/005
330/9
6,218,887 B1 * 4/2001 Brown ....................... H03F 3/72
327/408
(Continued)

FOREIGN PATENT DOCUMENTS

EP          2 893 873 A2    7/2015
JP          3417891 B2      6/2003
(Continued)

OTHER PUBLICATIONS

Yazicioglu, Refet Firat et al., "A 60 μW 60 nV/√Hz Readout Front-End for Portable Biopotential Acquisition Systems", *IEEE Journal of Solid-State Circuits*, vol. 42, No. 5, May 2007 (pp. 1100-1110).

(Continued)

*Primary Examiner* — Patricia T Nguyen
(74) *Attorney, Agent, or Firm* — NSIP Law

(57) ABSTRACT

Disclosed is a reconfigurable amplifier and an amplification method thereof, the amplifier includes an input selector, a first amplifying circuit, and a second amplifying circuit. The input selector is configured to select one of a voltage input and a current input based on a voltage measurement mode and a current measurement mode. The first amplifying circuit includes a first load element, and is configured to apply a voltage corresponding to the voltage input to the first load element in the voltage measurement mode and receive the current input in the current measurement mode and block a current flowing through the first load element. The second amplifying circuit is configured to mirror a current flowing through the first amplifying circuit in response to one of the voltage input and the current input and generate an output voltage based on the mirrored current.

26 Claims, 13 Drawing Sheets

(51) Int. Cl.
    *H03F 1/26*     (2006.01)
    *H03F 3/187*     (2006.01)
    *H03F 3/45*     (2006.01)
    *A61B 5/00*     (2006.01)
    *A61B 5/024*     (2006.01)

(52) U.S. Cl.
    CPC ........ *A61B 5/04288* (2013.01); *A61B 5/7225* (2013.01); *H03F 1/26* (2013.01); *H03F 3/187* (2013.01); *H03F 3/45475* (2013.01); *A61B 5/02416* (2013.01); *H03F 2200/231* (2013.01); *H03F 2200/249* (2013.01); *H03F 2200/252* (2013.01); *H03F 2200/261* (2013.01); *H03F 2200/372* (2013.01); *H03F 2200/462* (2013.01); *H03F 2200/471* (2013.01); *H03F 2200/75* (2013.01); *H03F 2203/45022* (2013.01); *H03F 2203/45258* (2013.01)

(56) References Cited

U.S. PATENT DOCUMENTS

| | | | |
|---|---|---|---|
| 6,340,909 B1* | 1/2002 | Zerbe | H03K 5/13 327/246 |
| 8,454,505 B2 | 6/2013 | Yazicioglu et al. | |
| 10,008,656 B1* | 6/2018 | Radhakrishnan | H01L 41/042 |
| 2005/0077972 A1* | 4/2005 | Oehm | H03B 5/129 331/36 C |
| 2008/0013577 A1* | 1/2008 | Saitoh | H01S 5/0683 372/38.01 |
| 2009/0093720 A1* | 4/2009 | Petersen | G01S 7/5208 600/447 |
| 2010/0263643 A1 | 10/2010 | Agneray et al. | |
| 2015/0335260 A1 | 11/2015 | Kim et al. | |
| 2016/0183884 A1 | 6/2016 | Lee et al. | |
| 2016/0331256 A1 | 11/2016 | Herleikson | |

FOREIGN PATENT DOCUMENTS

| | | |
|---|---|---|
| KR | 10-0670727 B1 | 6/2007 |
| KR | 10-1004851 B1 | 12/2010 |
| KR | 10-2015-0133631 A | 11/2015 |

OTHER PUBLICATIONS

Extended European Search Report dated Nov. 19, 2018 in corresponding European Application No. 18171430.4 (14 pages in English).

* cited by examiner

400

RECONFIGURABLE AMPLIFIER AND AMPLIFICATION METHOD THEREOF

CROSS-REFERENCE TO RELATED APPLICATIONS

This application claims the benefit under 35 USC § 119(a) of Korean Patent Application No. 10-2017-0097090 filed on Jul. 31, 2017 in the Korean Intellectual Property Office, the entire disclosure of which is incorporated herein by reference for all purposes.

BACKGROUND

1. Field

The following description relates to a reconfigurable amplifier and an amplification method thereof.

2. Description of Related Art

An instrumentation amplifier (IA) is used to measure various electrical signals. In a medical field, the IA may be used to measure a biosignal, for example, an electrocardiogram (ECG), an electromyogram (EMG), a photoplethysmogram (PPG), a body resistance, and a motion signal and amplify the measured biosignal. The IA may include a differential amplifier having a low offset, low noise, a high common mode rejection, a high loop gain, and a high input resistance.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In accordance with an example, there is provided an amplifier including: an input selector configured to select one of a voltage input and a current input based on a voltage measurement mode and a current measurement mode; a first amplifying circuit including a first load element, and configured to apply a voltage corresponding to the voltage input to the first load element in the voltage measurement mode and receive the current input in the current measurement mode and block a current flowing through the first load element; and a second amplifying circuit configured to mirror a current flowing through the first amplifying circuit in response to one of the voltage input and the current input and generate an output voltage based on the mirrored current.

The amplifier may further include: a current blocker connected to the first load element to be closed in the voltage measurement mode and open in the current measurement mode.

In response to the current flowing through the first load element being blocked in the current measurement mode, noise occurring in the output voltage due to a voltage applied to the first load element may be removed in the current measurement mode.

The input selector may further include: a voltage input selector configured to select the voltage input in the voltage measurement mode and select a preset reference voltage in the current measurement mode; and a current input selector configured to be open in the voltage measurement mode and select the current input in the current measurement mode.

The first amplifying circuit may further include a transconductance element operatively connecting the input selector to the first load element.

The transconductance element may be configured to generate a current corresponding to the voltage input in the voltage measurement mode, and the voltage corresponding to the voltage input may be applied to the first load element based on the generated current corresponding to the voltage input.

The second amplifying circuit may include a second load element to which at least a portion of the mirrored current may be applied, the output voltage may be determined in the voltage measurement mode based on a mirroring ratio of the mirrored current and a ratio between a value of the first load element and a value of the second load element, and the output voltage may be determined in the current measurement mode based on the mirroring ratio of the mirrored current and the value of the second load element.

The voltage input may correspond to an electrocardiogram (ECG) signal and the current input corresponds to a photoplethysmogram (PPG) signal.

The input selector may be configured to select the voltage input in a first time interval and select the current input in a second time interval, and the first time interval may not overlap with the second time interval.

During the first time interval of the control signal being a logical low, the second time interval of the control signal may be greater than the first time interval and the second time interval may be logical high.

The amplifier may further include: an analog-to-digital (ADC) converter configured to generate a first digital output based on the output voltage corresponding to the voltage input at a first point in time in the first time interval, and generate a second digital output based on the output voltage corresponding to the current input at a second point in time in the second time interval.

The second amplifying circuit may include: a first sub-amplifying circuit configured to output the output voltage based on the voltage input; and a second sub-amplifying circuit configured to output the output voltage based on the current input.

The amplifier may further include: a first sample and hold circuit configured to perform a sample and hold operation on the output voltage output from the first sub-amplifying circuit in a third time interval; and a second sample and hold circuit configured to perform a sample and operation on the output voltage output from the second sub-amplifying circuit in a fourth time interval, wherein the third time interval may be included in the first time interval and the fourth time interval may be included in the second time interval.

In accordance with an example, there is provided an amplification method, including: selecting one of a voltage input and a current input based on a measurement mode including a voltage measurement mode and a current measurement mode; controlling the voltage input to be applied to a load element; controlling the current input to be applied and a current flowing through the load element to be blocked; and generating an output voltage based on a mirrored current corresponding to one of the voltage input and the current input.

In response to the voltage input being selected, the controlling may include: applying the voltage input to the load element; and blocking the current input.

In response to the current input being selected, the controlling may include: blocking the voltage input and the current flowing through the load element; and receiving the current input.

In response to the current flowing through the load element being blocked in the current measurement mode, noise occurring in the output voltage due to a voltage applied to the load element may be removed.

The selecting may include: selecting the voltage input in a first time interval; and selecting a current input in a second time interval, and the first time interval may not overlap with the second time interval.

The generating of the output voltage may include: generating a first digital output based on the output voltage corresponding to the voltage input at a first point in time in the first time interval; and generating a second digital output based on the output voltage corresponding to the current input at a second point in time in the second time interval.

The amplification method may further include: performing a sample and hold operation on the output voltage based on the voltage input in a third time interval; and performing a sample and operation on the output voltage based on the current input in a fourth time interval, wherein the third time interval may be included in the first time interval and the fourth time interval may be included in the second time interval.

In accordance with an example, there is provided a signal processing apparatus including: a controller configured to output a control signal corresponding to one of a voltage measurement mode and a current measurement mode; and an amplifier configured to select one of a voltage input and a current input based on the control signal, control the voltage input to be applied to a load element, control the current input to be applied and a current flowing through the load element to be blocked, and generate an output voltage based on a mirrored current corresponding to one of the voltage input and the current input.

In accordance with an example, there is provided an amplifier, including: an input selector configured to select one of a voltage input in a voltage measurement mode, and a current input in the current measurement mode based on a control signal from a controller; a first amplifying circuit configured to, in the voltage measurement mode, receive the voltage input, generate a current corresponding to the voltage input, apply the voltage input a load element based on the current corresponding to the voltage input, and close a current blocker to block the current input, and in the current measurement mode, receive the current input and open the current blocker to block a current flowing through the load element to which the voltage input may be applied; and a second amplifying circuit configured to mirror the current flowing through the first amplifying circuit based on one of the voltage input and the current input, and generate an output voltage based on the mirrored current.

The second amplifying circuit may include a second load element, and at least a portion of the mirrored current may be applied to the second load element.

In the voltage measurement mode, the output voltage may be based on a mirroring ratio of the mirrored current, and a ratio between a value of the first load element and a value of the second load element.

In the current measurement mode, the output voltage may be determined based on a mirroring ratio of the mirrored current and the value of the second load element.

Other features and aspects will be apparent from the following detailed description, the drawings, and the claims.

BRIEF DESCRIPTION OF THE DRAWINGS

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

Although terms such as "first," "second," and "third" may be used herein to describe various members, components, regions, layers, or sections, these members, components, regions, layers, or sections are not to be limited by these terms. Rather, these terms are only used to distinguish one member, component, region, layer, or section from another member, component, region, layer, or section. Thus, a first member, component, region, layer, or section referred to in examples described herein may also be referred to as a second member, component, region, layer, or section without departing from the teachings of the examples.

The terminology used herein is for describing various examples only, and is not to be used to limit the disclosure. The articles "a," "an," and "the" are intended to include the plural forms as well, unless the context clearly indicates otherwise. The terms "comprises," "includes," and "has" specify the presence of stated features, numbers, operations, members, elements, and/or combinations thereof, but do not preclude the presence or addition of one or more other features, numbers, operations, members, elements, and/or combinations thereof.

Unless otherwise defined, all terms, including technical and scientific terms, used herein have the same meaning as commonly understood by one of ordinary skill in the art to which this disclosure pertains. Terms, such as those defined in commonly used dictionaries, are to be interpreted as having a meaning that is consistent with their meaning in the context of the relevant art, and are not to be interpreted in an idealized or overly formal sense unless expressly so defined herein.

Figure 1:
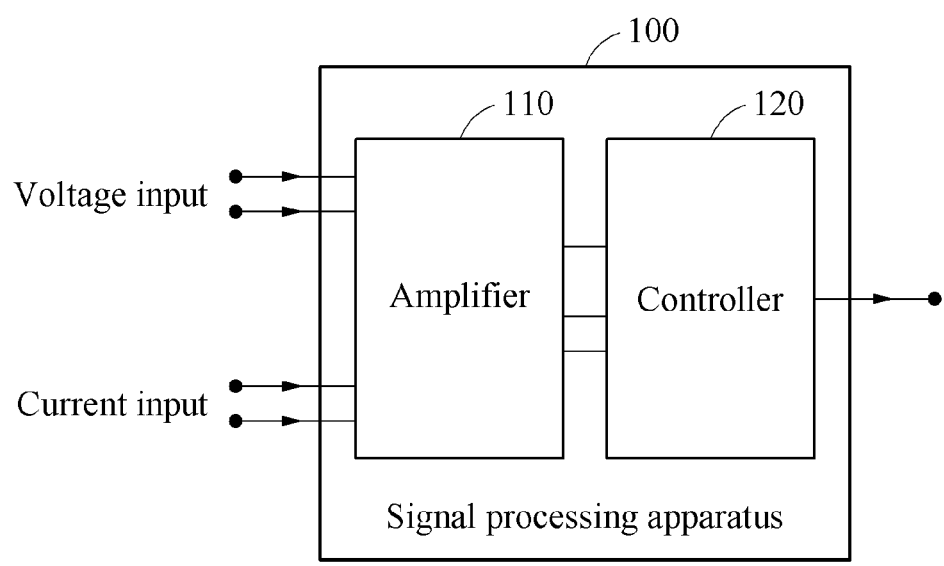
FIG. 1 illustrates an example of signal processing apparatus.

FIG. 1 is a block diagram illustrating an example of a signal processing apparatus. Referring to FIG. 1, a signal processing apparatus 100 includes an amplifier 110 and a controller 120.

The signal processing apparatus 100 measures an input voltage and an input current based on a single integrated circuit configuration. The signal processing apparatus 100 operates in a measurement mode including a voltage measurement mode and a current measurement mode. The signal processing apparatus 100 measures a voltage input in the voltage measurement mode and measures a current input in the current measurement mode. For example, the signal processing apparatus 100 time-divisionally measures the voltage input and the current input by alternating the measurement of the voltage input and the current input during or at a predetermined time, or at predetermined time intervals or periods. In an alternative example, the voltage input and the current input may be measured simultaneously. A measurement mode in which the voltage input and the current input are simultaneously measured is referred to as, for example, a combined measurement mode. The controller 120 generates a control signal corresponding to the measurement mode of the signal processing apparatus 100. The signal processing apparatus 100 provides a compatibility of measuring both voltage and current and outputs the control signal from the controller 120 indicative of the measurement of the voltage and the current.

The signal processing apparatus 100 operates as an instrumentation amplifier (IA). The signal processing apparatus 100 is used to measure a biosignal. For example, the signal processing apparatus 100 includes an amplifier 110 to amplify a voltage measurement based biosignal such as an electrocardiogram (ECG) in the voltage measurement mode and amplify a current measurement based biosignal, such as a photoplethysmogram (PPG), in the current measurement mode. The signal processing apparatus 100 measures the ECG in the voltage measurement mode and the PPG in the current measurement mode. In FIG. 1, the voltage input corresponds to an ECG signal measured from a body of a user. Also, the current input corresponds to a PPG signal measured from the body of the user. Types of the voltage input and the current input are not limited to the foregoing example and, thus, may include various biosignals.

The controller 120 generates the control signal corresponding to the measurement mode of the signal processing apparatus 100 and provides the control signal to the amplifier 110. The amplifier 110 amplifies at least one of the input voltage and the input current based on the control signal output from the controller 120. For example, the amplifier 110 amplifies one of the input voltage and the input current, or simultaneously amplifies the input voltage and the input current. In this example, the simultaneously amplifying the input voltage and the input current may be understood as time-divisionally amplifying the input voltage and the input current together. In another example, the input voltage and the input current are time-divisionally amplified in an alternating manner.

The amplifier 110 selects one of the voltage input and the current input by performing a switching operation in response to the control signal. For example, in the voltage measurement mode, the amplifier 110 selects the voltage input and blocks an inflow of the current input. In the current measurement mode, the amplifier 110 selects the current input and blocks an inflow of the voltage input. Also, in the combined measurement mode, the amplifier 110 alternately selects the voltage input and the current input. In one example, the voltage input and the current input may be provided as differential signals. In this example, the amplifier 110 operates as a differential amplifier.

The amplifier 110 cancels an interference occurring between a voltage measuring element and a current measuring element. For example, in response to selecting the voltage input, the amplifier 110 amplifies the voltage input using a load element to measure voltage. In this example, the amplifier 110 blocks the current input and, thus, a current flowing into or through the load element while measuring the voltage to prevent noise occurring due to the load element. Through this, a measurement performance of the amplifier 110 is improved.

The selection of the voltage input or the current input, that is, measurement mode of the signal processing apparatus 100, is determined or performed by an external device. For example, the external device includes the signal processing apparatus 100, and the signal processing apparatus 100 amplifies a signal selected by the external device and transmits the amplified signal to the external device. The external device may include an electronic device, for example, a smartphone, a wearable device, and a medical instrument. The external device requests or selects at least one of the voltage input and the current input to the signal processing apparatus 100. In response to a request from the external device, the controller 120 generates the control signal.

The amplifier 110 generates an output signal by amplifying the requested or the selected voltage input or current input. The controller 120 receives the output signal from the amplifier 110 and determines a measured value corresponding to the output signal. When the voltage input corresponds to an ECG signal, the controller 120 determines a measured value of the ECG signal based on the output signal from the amplifier 110. When the current input corresponds to a PPG signal, the controller 120 determines a measured value of the PPG signal based on the output signal from the amplifier 110.

Figure 2:
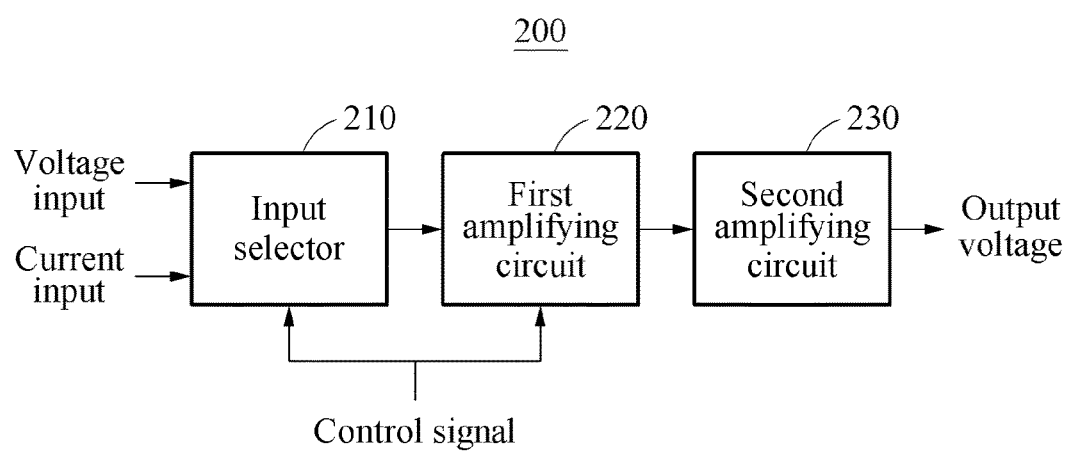
FIG. 2 illustrates an example of an amplifier.

FIG. 2 is a block diagram illustrating an example of an amplifier. Referring to FIG. 2, an amplifier 200 includes an input selector 210, a first amplifying circuit 220, and a second amplifying circuit 230.

The input selector 210 selects one of a voltage input and a current input based on a measurement mode. The input selector 210 includes a switching element to select one of the voltage input and the current input and operates the switching element based on a control signal from a controller (such as the controller 120 of FIG. 1). The measurement mode is determined based on the control signal. When the control signal indicates a voltage measurement mode, the input selector 210 selects the voltage input. When the control signal indicates a current measurement mode, the input selector 210 selects the current input.

The measurement mode is determined based on a level of the control signal. For example, the voltage measurement mode is determined based on a first level of the control signal, and the current measurement mode is determined based on a second level of the control signal. Different control signals may be used to determine the measurement mode. For example, the voltage measurement mode is determined based on a first level of a first control signal, and the current measurement mode is determined based on a second level of a second control signal. In this example, the first level corresponds to one of "logical high" and "logical low" and the second level corresponds to the other of "logical high" and "logical low".

The input selector 210 includes a voltage input selector and a current input selector. The voltage input selector selects the voltage input in a voltage measurement mode based on the control signal and selects a preset reference voltage in a current measurement mode. The current input selector is opened (that is, "logical low") in the voltage measurement mode based on the control signal. In the current measurement mode, the current input selector selects the current input (that is, "logical high"). As discussed below, the first amplifying circuit 220 includes a transconductance element configured to receive the voltage input in the voltage measurement mode. The preset reference voltage is used to enable the transconductance element to operate in a predetermined operation range in the current measurement mode.

The first amplifying circuit 220 receives the voltage input or the current input based on a selection of the input selector 210. For example, the first amplifying circuit 220 receives the voltage input in the voltage measurement mode or receives the current input in the current measurement mode. The first amplifying circuit 220 operates based on the control signal. The measurement mode is determined based on the control signal.

Each of the first amplifying circuit 220 and the second amplifying circuit 230 includes a load element. Hereinafter, a load element included in the first amplifying circuit 220 is referred to as a first load element, and a load element included in the second amplifying circuit 230 is referred to as a second load element. The first amplifying circuit 220 applies a voltage corresponding to the voltage input to the first load element in the voltage measurement mode and receives the current input in the current measurement mode in a state in which a current flowing through the first load element is blocked. The first amplifying circuit 220 includes a current blocker. The current blocker is connected to the first load element of the first amplifying circuit 220 to be a short or closed in the voltage measurement mode and open in the current measurement mode. In response to the current flowing through the first load element being blocked, noise occurring in an output voltage due to the voltage applied to the first load element in the current measurement mode is removed.

In one configuration, although the input selector 210 is shown to be structurally separate and operatively connected to the first amplifying circuit 220, the input selector 210 may be integrated or part of the first amplifying circuit 220.

The first amplifying circuit 220 includes the transconductance element connected to the first load element. The transconductance element generates a current corresponding to the voltage input in the voltage measurement mode. The voltage corresponding to the voltage input is applied to the first load element based on the current corresponding to the voltage input generated by the transconductance element. The first amplifying circuit 220 will also be described with reference to FIG. 3.

The second amplifying circuit 230 is operatively connected to the first amplifying circuit 220. The second amplifying circuit 230 mirrors the current flowing through the first amplifying circuit 220 based on one of the voltage input (when operating in the voltage measurement mode) and the current input (when operating in the current measurement mode), and generates an output voltage based on the mirrored current. At least a portion of the mirrored current is applied to the second load element in the second amplifying circuit 230. In the voltage measurement mode, the output voltage is determined based on a mirroring ratio of the mirrored current, and a ratio between a value of the first load element and a value of the second load element. In the current measurement mode, the output voltage is determined based on the mirroring ratio of the mirrored current and the value of the second load element. Although the second amplifying circuit 230 is structurally external to and operatively connected to the first amplifying circuit 220, in an alternative example, the first and second amplifying circuits 220 and 230 may be integrated as one structural element. The second amplifying circuit 230 will also be described with reference to FIG. 4.

Figure 3:
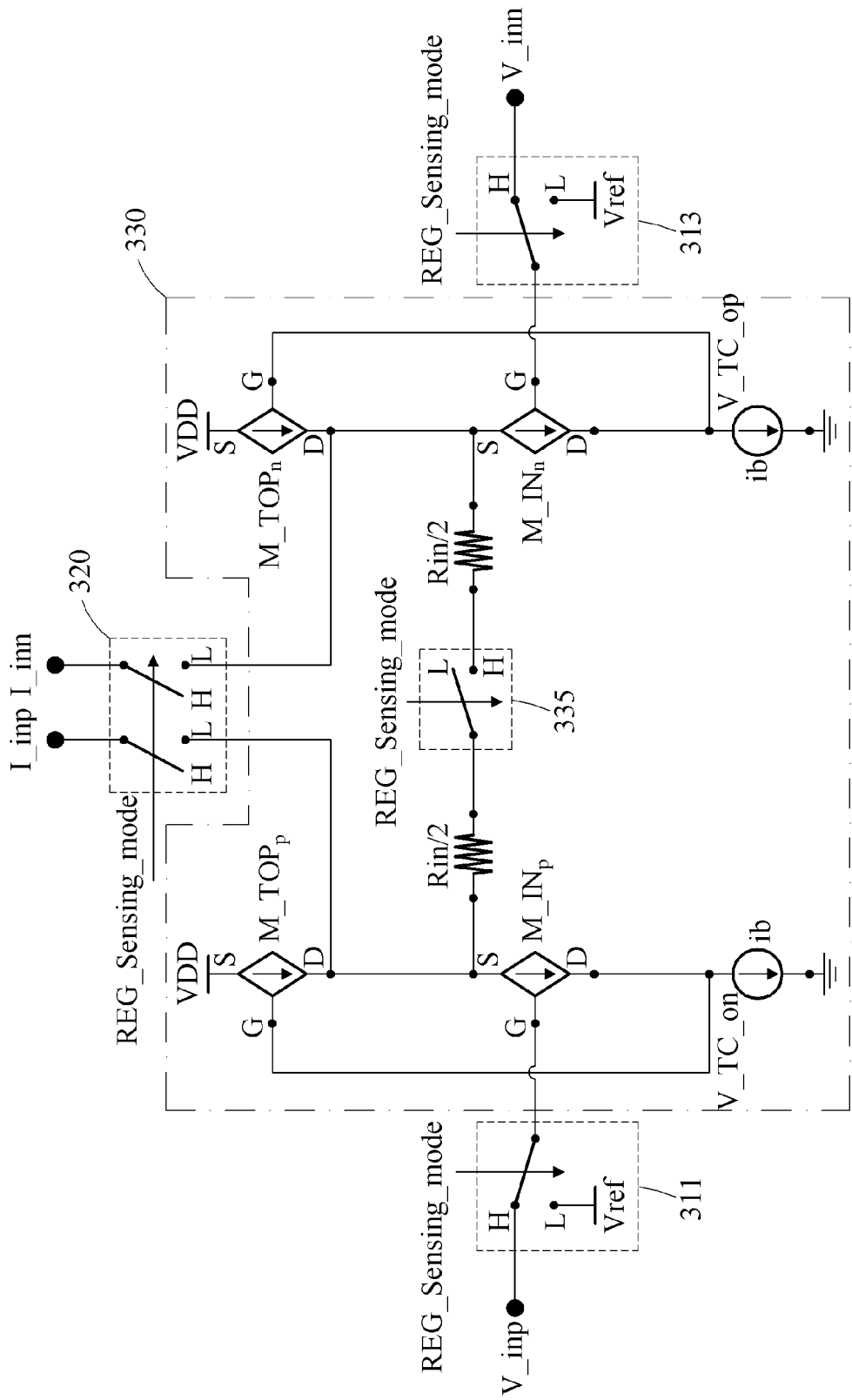
FIG. 3 illustrates an example of an input selector and a first amplifying circuit.

FIG. 3 is a circuit diagram illustrating an example of an input selector and a first amplifying circuit. Referring to FIG. 3, input voltage selectors 311 and 313, an input current selector 320, and a first amplifying circuit 330 are illustrated. The input voltage selectors 311 and 313 and the input current selector 320 are included in an input selector.

The input voltage selectors 311 and 313 receive voltage inputs V_inp and Vinn. The input current selector 320 receives current inputs I_inp and I_inn. The voltage inputs V_inp and Vinn, and the current inputs I_inp and I_inn each may be a differential signal. The input voltage selector 311 selects one of the voltage input V_inp and a reference voltage Vref based on a control signal REG_Sensing_mode. The input current selector 320 selects the current inputs I_inp and I_inn or is opened based on the control signal REG_Sensing_mode. In an example of FIG. 3, a level of the control signal REG_Sensing_mode is "logical high" in a voltage measurement mode and "logical low" in the current measurement mode. The level of the control signal REG_Sensing_mode is not limited to the foregoing example. In an alternative example, the level of the control signal REG_Sensing_mode is "logical low" in the voltage measurement mode and "logical high" in the current measurement mode.

The first amplifying circuit 330 includes transconductance elements M_TOP_p, M_TOP_n, M_IN_p, and M_IN_n, a constant current source ib, a load element Rin, and a current blocker 335. The load element Rin corresponds to the aforementioned first load element. Although FIG. 3 illustrates each of the transconductance elements M_TOP_p, M_TOP_n, M_IN_p, and M_IN_n as a single symbol, each of the transconductance elements M_TOP_p, M_TOP_n, M_IN_p, and M_IN_n may include at least one more transconductance element. Each of the transconductance elements M_TOP_p, M_TOP_n, M_IN_p, and M_IN_n generates a current based on a gate-source voltage. Thus, each of the transconductance elements M_TOP_p, M_TOP_n, M_IN_p, and M_IN_n operates as a voltage controlled current source.

Hereinafter, the first amplifying circuit 330 operating in the voltage measurement mode and the current measurement mode will be described.

<Voltage Measurement Mode>

In the voltage measurement mode, the voltage input V_inp is applied to a gate of the transconductance element M_IN_p, and the transconductance element M_IN_p generates a current corresponding to the voltage input V_inp. Similarly, in the voltage measurement mode, the voltage input V_inn is applied to a gate of the transconductance element M_IN_n, and the transconductance element M_IN_n generates a current corresponding to the voltage input V_inn.

Using the constant current source ib and the transconductance elements M_TOP_p and M_TOP_n, the currents corresponding to the voltage inputs V_inp and V_inn are applied to the load element Rin. Thus, voltages corresponding to the voltage inputs V_inp and V_inn are applied to the load element Rin based on the currents corresponding to the voltage inputs V_inp and V_inn generated by the transconductance elements M_IN_p and M_IN_n. A predetermined difference in level may be maintained between the voltage inputs V_inp and V_inn and the voltages applied to the load element Rin.

In the voltage measurement mode, the current blocker 335 is a short or closed based on the control signal REG_Sensing_mode. As a result, the voltages corresponding to the voltage inputs V_inp and V_inn are applied to the load element Rin.

<Current Measurement Mode>

In the current measurement mode, the current inputs I_inp and I_inn flow into the first amplifying circuit 330. Also, in the current measurement mode, the reference voltage Vref is applied to a gate of the transconductance element M_IN_p and the transconductance element M_IN_p generates a current corresponding to the reference voltage Vref. Similarly, in the voltage measurement mode, the reference voltage Vref is applied to a gate of the transconductance element M_IN_n and the transconductance element M_IN_n generates a current corresponding to the reference voltage Vref. The reference voltage Vref is set or defined to be a voltage at which the transconductance elements M_IN_p and M_IN_n operate within a designed operation range.

The current blocker 335 is open (that is, "logical low") based on the control signal REG_Sensing_mode in the current measurement mode. Thus, in the current measurement mode, the load element Rin does not affect an operation of the first amplifying circuit 330. When a voltage is applied to the load element Rin in the current measurement mode, noise may occur in an output voltage. In this example, in response to the current blocker 335 being open, the noise occurring in the output voltage due to the voltage applied to the load element Rin is removed.

Hereinafter, an operation of the first amplifying circuit 330 will be described. A voltage V_TC_on is applied to a gate of the transconductance element M_TOP_p and a voltage VDD is applied to a source of the transconductance element M_TOP_p. Similarly, a voltage V_TC_op is applied to a gate of the transconductance element M_TOP_n and the voltage VDD is applied to a source of the transconductance element M_TOP_n. Each of the transconductance elements M_IN_p and M_TOP_n generates a current based on a gate-source voltage. The current generated by each of the transconductance elements M_IN_p and M_TOP_n is mirrored to a second amplifying circuit. The second amplifying circuit generates an output voltage based on the mirrored current. The second amplifying circuit will be described with reference to FIG. 4.

Figure 4:
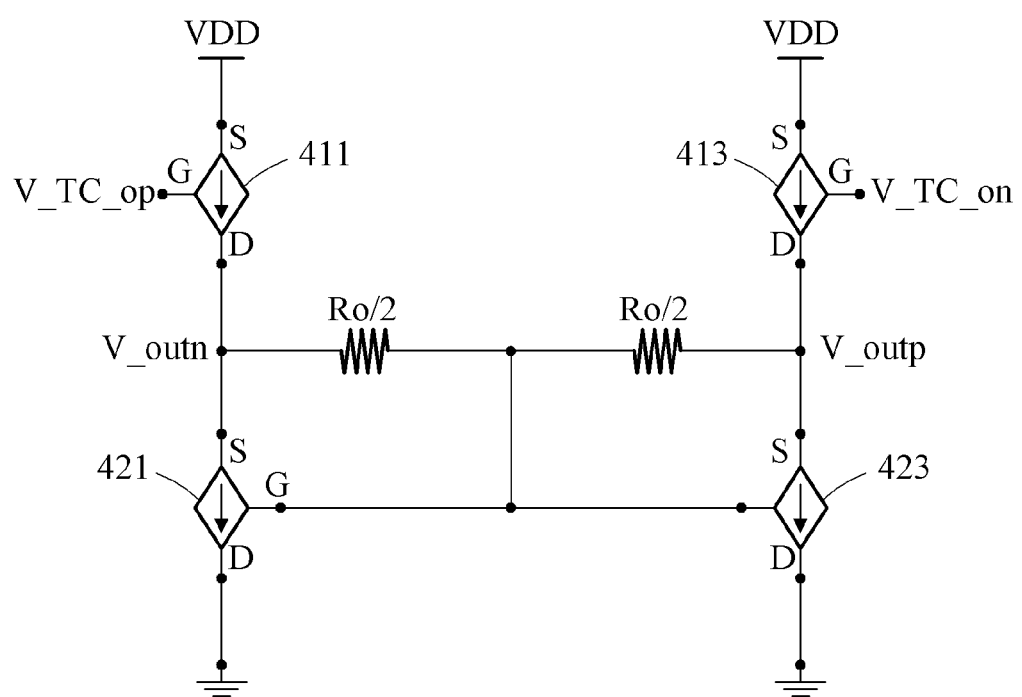
FIG. 4 illustrates an example of a second amplifying circuit.

FIG. 4 is a circuit diagram illustrating an example of a second amplifying circuit. Referring to FIG. 4, a second amplifying circuit 400 includes transconductance elements 411, 413, 421, and 423, and a load element Ro. The load element Ro corresponds to the aforementioned second load element.

A voltage V_TC_op is applied to a gate of the transconductance element 411 and a voltage VDD is applied to a source of the transconductance element 411. Similarly, a voltage V_TC_on is applied to a gate of the transconductance element 413 and the voltage VDD is applied to a source of the transconductance element 413. The transconductance elements 411 and 413 mirror the currents generated by the transconductance elements M_IN_p and M_TOP_n of FIG. 3 in the second amplifying circuit 400. Hereinafter, currents generated by the transconductance elements 411 and 413 are referred to as mirrored currents. A predetermined ratio between the mirrored currents and the currents generated by the transconductance elements M_IN_p and M_TOP_n is formed. The ratio is referred to as a mirroring ratio α.

At least a portion of output voltages V_outn and V_outp is applied to the gates of the transconductance elements 421 and 423, and the output voltages V_outn and V_outp are applied to the sources of the transconductance elements 421 and 423. Each of the transconductance elements 421 and 423 generates a current based on a gate-source voltage. The transconductance elements 421 and 423 form the output voltages V_outn and V_outp in a predefined operation range.

The second amplifying circuit 400 generates the output voltages V_outn and V_outp based on the mirrored current. At least a portion of the mirrored current is applied to the load element Ro. In a voltage measurement mode, a ratio corresponding to the mirroring ratio α is formed between the current flowing through the load element Ro and the current flowing through the load element Ri of FIG. 3 due to the transconductance elements 421 and 423. In this example, the current flowing through the load element Ri is mirrored to the load element Ro. Thus, the output voltages V_outn and V_outp are determined based on the mirroring ratio α, and a ratio between a value of the load element Ri and a value of the load element Ro in the voltage measurement mode. As described above, the load element Ri does not affect the output voltages V_outn and V_outp in a current measurement mode. Thus, in the current measurement mode, the output voltages V_outn and V_outp are determined based on the mirroring ratio α and the value of the load element Ro.

As described with reference to FIGS. 2 through 4, the amplifier 110 or 200 generates an output voltage by amplifying a voltage input in a voltage measurement mode or generates an output voltage by amplifying a current input in a current measurement mode. For example, the amplifier time-divisionally amplifies the voltage input and the current input at different times. The amplifier performs such operation in a combined measurement mode. Hereinafter, an operation of an amplifier simultaneously measuring a voltage input and a current input will be described with reference to FIGS. 5 through 10.

Figure 5:
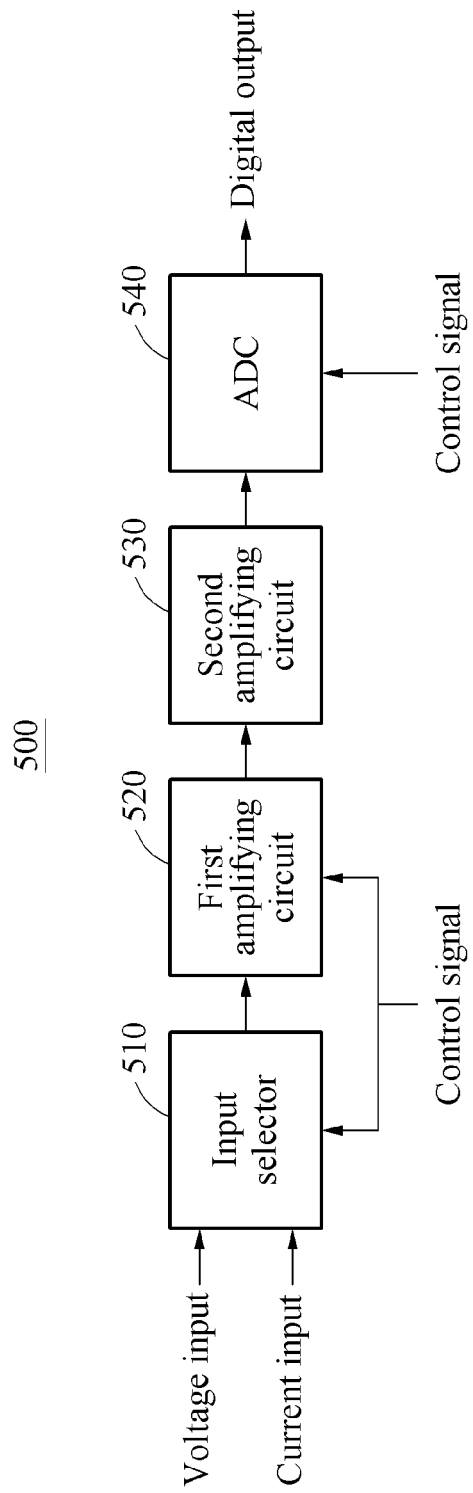
FIG. 5 illustrates an example of an amplifier.

FIG. 5 is a block diagram illustrating an example of an amplifier. Referring to FIG. 5, an amplifier 500 includes an input selector 510, a first amplifying circuit 520, a second amplifying circuit 530, and an analog-to-digital converter (ADC) 540.

Each of the input selector 510, the first amplifying circuit 520, and the ADC 540 operate based on a control signal. The input selector 510 includes an input voltage selector and an input current selector. In an example, a control signal input to the input voltage selector is referred to as a first control signal, a control signal input to the input current selector is referred to as a second control signal, and a control signal input to the ADC 540 is referred to as a third control signal. The control signal input to the first amplifying circuit 520 is the first control signal or the second control signal.

The input selector 510 selects a voltage input in a first time interval and selects a current input in a second time interval. In one example, the first time interval does not overlap the second time interval. The first time interval indicates an interval in which a first level of the first control signal is maintained. The second time interval indicates an interval in which a first level of the second control signal is maintained. The first level corresponds to, for example, "logical high". The control signal provided to the amplifier 500 will also be described with reference to FIG. 7.

Based on an operation of the input selector 510, a voltage input and a current input are alternately applied to the first amplifying circuit 520. The second amplifying circuit 530 generates an output voltage by mirroring a current flowing through the first amplifying circuit 520. The second amplifying circuit 530 generates an output voltage alternatively corresponding to the voltage input and an output voltage corresponding to the current input. The first amplifying circuit 520 includes a current blocker and the first control signal is provided to the current blocker. In the output voltage corresponding to the current input, noise occurring due to a load element in the first amplifying circuit 520 is removed.

The ADC 540 generates a digital output based on an output voltage output from the second amplifying circuit 530. The ADC 540 generates a first digital output based on the output voltage corresponding to the voltage input at a first point in time in the first time interval. Also, the ADC 540 generates a second digital output based on the output voltage corresponding to the current input at a second point in time in the second time interval. The digital output includes a first component corresponding to the voltage input and a second component corresponding to the current input. By extracting the first component and the second component, an amplified value of the voltage input and an amplified value of the current input are restored.

Because the description of FIG. 2 is also applicable here, repeated description with respect to the input selector 510, the first amplifying circuit 520, and the second amplifying circuit 530 will be omitted for brevity.

Figure 6:
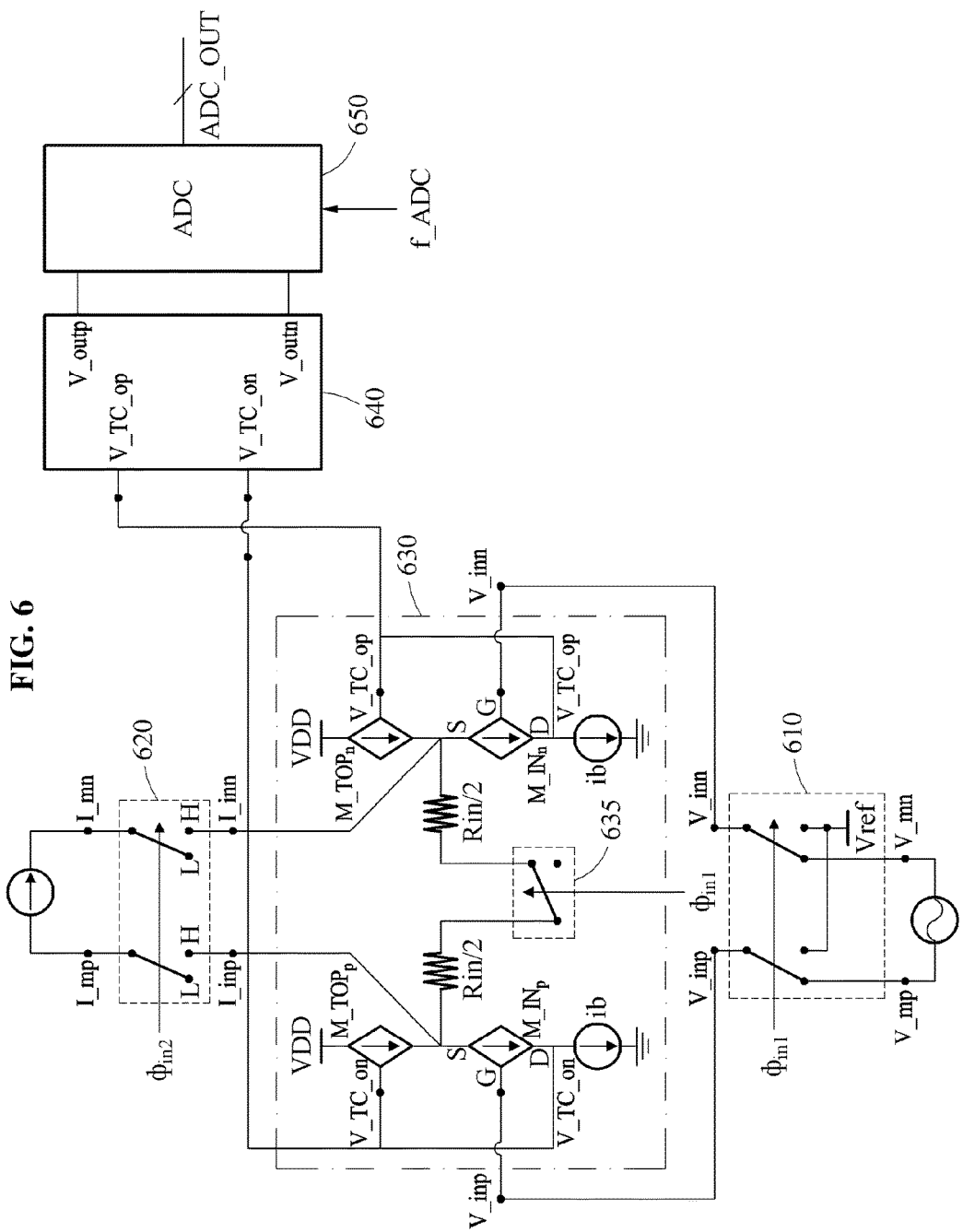
FIG. 6 illustrates an example of an amplifier.

FIG. 6 is a circuit diagram illustrating an example of an amplifier. Referring to FIG. 6, a voltage input selector 610, a current input selector 620, a first amplifying circuit 630, a second amplifying circuit 640, and an ADC 650 are illustrated.

The voltage input selector 610 selects one of voltage inputs V_mp and V_mn and a reference voltage Vref based on a control signal φ_in1. Based on an operation of the voltage input selector 610, voltage inputs V_inp and V_inn are applied to the first amplifying circuit 630. The current input selector 620 selects current inputs I_mp and I_mn or is open based on a control signal φ_in2. Based on an operation of the current input selector 620, current inputs I_inp and I_inn are supplied to the first amplifying circuit 630.

A first level of the control signal φ_in1 does not overlap a first level of the control signal φ_in2. The control signal φ_in1 is set to be at the first level in a voltage measurement mode. The control signal φ_in2 is set to be at the first level in a current measurement mode. The voltage inputs V_mp and V_mn, and the current inputs I_mp and I_mn are alternately applied to the first amplifying circuit 630. Based on the control signal φ_in1, a current blocker 635 is a short or closed in the voltage measurement mode and is open in the current measurement mode.

The second amplifying circuit 640 mirrors currents generated by the transconductance elements M_IN_p and M_TOP_n based on voltages V_TC_op and V_TC_on. Also, the second amplifying circuit 640 generates output voltages V_outp and V_outn based on the mirrored currents. In response to the control signal φ_in1 corresponding to the first level, the second amplifying circuit 640 generates the output voltages V_outp and V_outn corresponding to the voltage inputs V_mp and V_mn. In response to the control signal φ_in2 corresponding to the first level, the second amplifying circuit 640 generates the output voltages V_outp and V_outn corresponding to the current inputs I_mp and I_mn.

The ADC 650 generates a digital output ADC_OUT corresponding to the output voltages V_outp and V_outn based on a control signal f_ADC. The digital output ADC_OUT includes a first component corresponding to the voltage inputs V_mp and V_mn and a second component corresponding to the current inputs I_mp and I_mn. By extracting the first component and the second component from the digital output ADC_OUT, amplified values of the voltage inputs V_mp and V_mn and amplified values of the current inputs I_mp and I_mn are restored.

Because the description of FIGS. 3 and 4 is also applicable here, repeated description with respect to the voltage input selector 610, the current input selector 620, the first amplifying circuit 630, and the second amplifying circuit 640 will be omitted for brevity.

Figure 7:
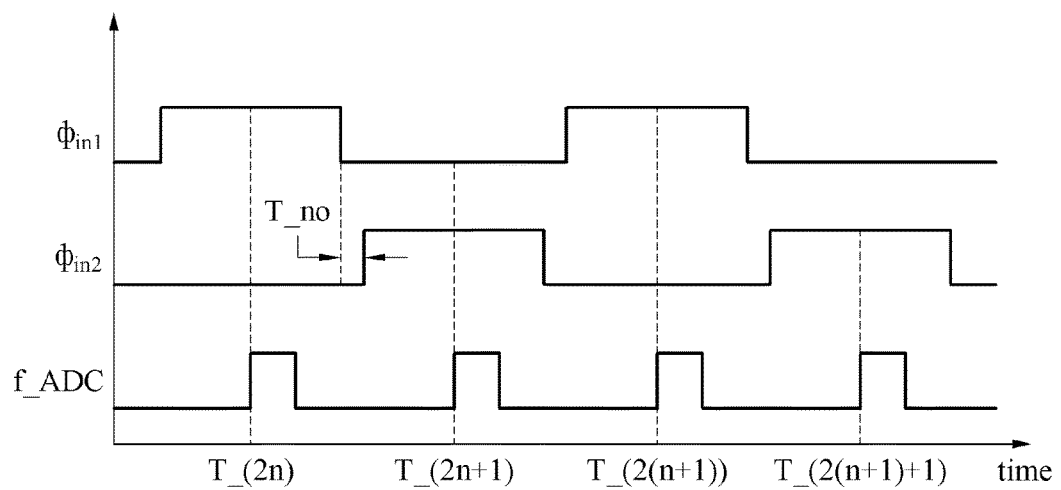
FIG. 7 illustrates an example of a control signal of an amplifier.

FIG. 7 is a timing diagram illustrating an example of a control signal of an amplifier. Referring to FIG. 7, waveforms of a control signal φ_in1, a control signal φ_in2, and a control signal f_ADC are illustrated.

As further discussed with reference to FIG. 5, a first time interval corresponds to an interval in which a level of the control signal φ_in1 is "logical high", and a second time interval corresponds to an interval in which a level of the control signal φ_in2 is "logical high". The first time interval does not overlap the second time interval. For example, a time T_no is greater than 0. In an example, the first time interval of the control signal φ_in1 being a "logical low" is greater than the second time interval of the control signal φ_in2 being "logical high". The first point in time of FIG. 5 corresponds to a rising edge of the control signal f_ADC in the first time interval. Also, the second point in time of FIG. 5 corresponds to a rising edge of the control signal f_ADC in the second time interval.

Based on the control signal φ_in1 and the control signal φ_in2, an output voltage corresponding to a voltage input is supplied to an ADC in the first time interval. The ADC generates a first digital signal corresponding to the voltage input at the first point in time. Also, based on the control signal φ_in1 and the control signal φ_in2, an output voltage corresponding to a current input is supplied to the ADC in the second time interval. The ADC generates a second digital signal corresponding to the current input at the second point in time. An amplified value corresponding to the voltage input and an amplified value corresponding to the current input are restored based on the digital output of the ADC.

Figure 8:
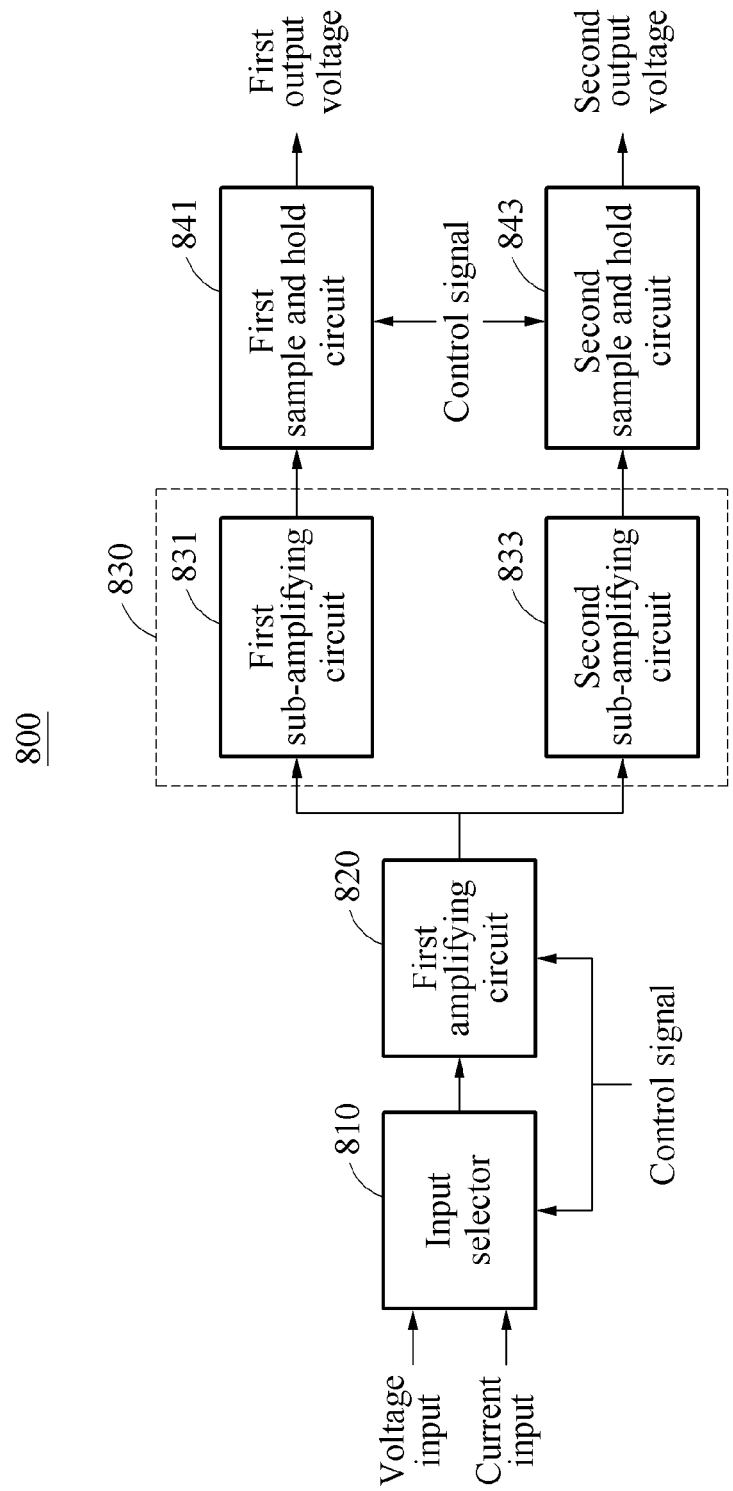
FIG. 8 illustrates an example of an amplifier.

FIG. 8 is a block diagram illustrating an example of an amplifier. Referring to FIG. 8, an amplifier 800 includes an input selector 810, a first amplifying circuit 820, a first sub-amplifying circuit 831, a second sub-amplifying circuit 833, a first sample and hold circuit 841, and a second sample and hold circuit 843. The first sub-amplifying circuit 831 and the second sub-amplifying circuit 833 may be included in a second amplifying circuit 830.

Each of the input selector 810, the first amplifying circuit 820, the first sample and hold circuit 841, and the second sample and hold circuit 843 operates based on a control signal. The input selector 810 includes an input voltage selector and an input current selector. Hereinafter, a control signal input to the input voltage selector is referred to as a first control signal, a control signal input to the input current selector is referred to as a second control signal, a control signal input to the first sample and hold circuit 841 is referred to as a third control signal, and a control signal input to the second sample and hold circuit 843 is referred to as a fourth control signal.

The input selector 810 selects a voltage input in a first time interval and selects a current input in a second time interval. Because the description of FIGS. 5 through 7 is also applicable here, repeated description with respect to the first time interval and the second time interval will be omitted for brevity.

Based on an operation of the input selector 810, the voltage input and the current input are alternately applied to the first amplifying circuit 820. The first sub-amplifying circuit 831 generates an output voltage based on the voltage input. The second sub-amplifying circuit 833 generates an output voltage based on the current input. The first sub-amplifying circuit 831 generates the output voltage by mirroring a current flowing through the first amplifying circuit 820 based on the voltage input. The second sub-amplifying circuit 833 generates the output voltage by mirroring a current flowing through the first amplifying circuit 820 based on the current input. The first amplifying circuit 820 includes a current blocker, and the first control signal is provided to the current blocker. Through this, noise occurring due to a load element of the first amplifying circuit 820 is removed from the output voltage corresponding to the current input.

The first sample and hold circuit 841 performs a sample and hold operation on the output voltage output from the first sub-amplifying circuit 831 in a third time interval. The second sample and hold circuit 843 performs the sample and hold operation on the output voltage output from the second sub-amplifying circuit 833 in a fourth time interval. The third time interval is included in the first time interval and the fourth time interval is included in the second time interval. A control signal provided to the amplifier 800 will also be described with reference to FIG. 10.

Because the output voltage of the first sub-amplifying circuit 831 is generated based on the voltage input, a first output voltage of the first sample and hold circuit 841 corresponds to the voltage input. Also, because the output voltage of the second sub-amplifying circuit 833 is generated based on the current input, a second output voltage of the second sample and hold circuit 843 corresponds to the current input. Thus, an amplified value of the voltage input and an amplified value of the current input are determined based on the first output voltage and the second output voltage.

Because the description of FIG. 2 is also applicable here, repeated description with respect to the input selector 810, the first amplifying circuit 820, the first sub-amplifying circuit 831, and the second sub-amplifying circuit 833 will be omitted for brevity.

Figure 9:
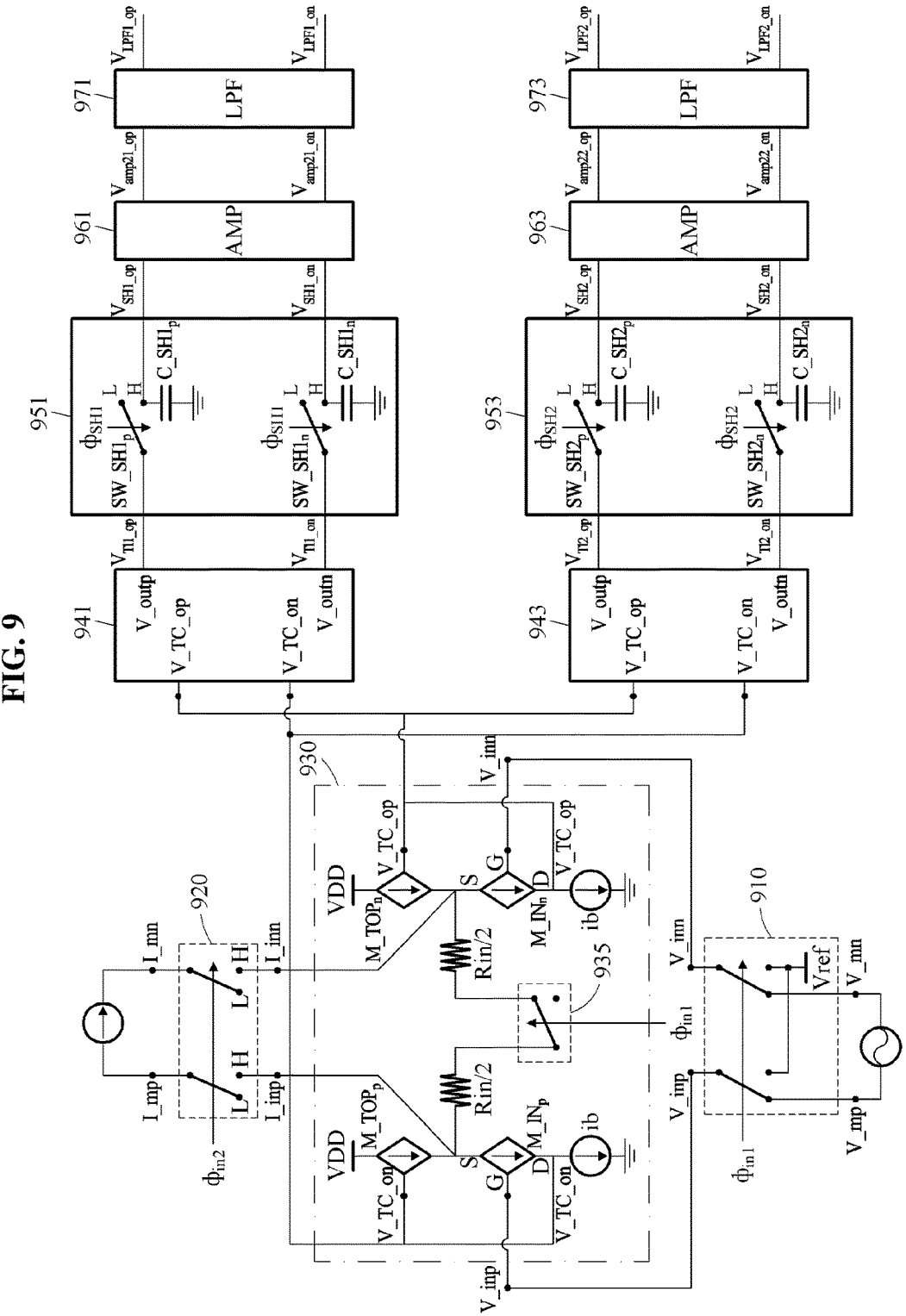
FIG. 9 illustrates an example of an amplifier.

FIG. 9 is a circuit diagram illustrating an example of an amplifier. Referring to FIG. 9, a voltage input selector 910, a current input selector 920, a first amplifying circuit 930, a first sub-amplifying circuit 941, a second sub-amplifying circuit 943, a first sample and hold circuit 951, a second sample and hold circuit 953, an amplifier 961, an amplifier 963, a low pass filter 971, and a low pass filter 973. The first amplifying circuit 930 includes a current blocker 935.

The voltage input selector 910 selects one of voltage inputs V_mp and V_mn and a reference voltage Vref based on a control signal φ_in1. The current input selector 920 selects current inputs I_mp and I_mn or is opened based on a control signal φ_in2. The current blocker 935 is a short or closed in a voltage measurement mode and is open in a current measurement mode based on the control signal φ_in1. Because the description of FIG. 6 is also applicable here, repeated description with respect to the voltage input selector 910, the current input selector 920, and the first amplifying circuit 930 will be omitted for brevity.

The first sub-amplifying circuit 941 mirrors currents generated by transconductance elements M_IN_p and M_TOP_n based on voltages V_TC_op and V_TC_on, and generates output voltages V_outp and V_outn based on the mirrored current. In response to the control signal φ_in1 corresponding to a first level, the first sub-amplifying circuit 941 generates the output voltages V_outp and V_outn corresponding to the voltage inputs V_mp and V_mn. As illustrated in FIG. 9, voltages V_TI1_op and V_TI1_on are the output voltages V_outp and V_outn corresponding to the voltage inputs V_mp and V_mn.

The first sample and hold circuit 951 includes a switching element SW_SH1p, a switching element SW_SH1n, a capacitive element C_SH1p, and a capacitive element C_SH1n. The switching element SW_SH1p and the switching element SW_SH1n apply the voltages V_TI1_op and V_TI1_on to the capacitive element C_SH1p and the capacitive element C_SH1n based on the control signal φ_SH1. For example, in response to the control signal φ_SH1 corresponding to a first level, the capacitive element C_SH1p and the capacitive element C_SH1n are charged at the voltages V_TI1_op, V_TI1_on. The first sample and hold circuit 951 outputs voltages V_SH1_op and V_SH1_on based on charges in the capacitive element C_SH1p and the capacitive element C_SH1n, respectively.

The amplifier 961 amplifies the voltages V_SH1_op and V_SH1_on to be voltages V_amp21_op and V_amp21_on, respectively. The low pass filter 971 filters the voltages V_amp21_op and V_amp21_on and outputs voltages V_LPF1_op and V_LPF1_on, respectively. Amplified values of the voltage inputs V_mp and V_mn are determined based on the voltages V_LPF1_op and V_LPF1_on. For example, the amplifier 961 and the low pass filter 971 are not used. In this example, the amplified values of the voltage inputs V_mp and V_mn are determined based on the voltages V_SH1_op and V_SH1_on.

In response to the control signal φ_in2 corresponding to the first level, the second sub-amplifying circuit 943 generates the output voltages V_outp and V_outn corresponding to the current inputs I_mp and I_mn. As illustrated in FIG. 9, voltages V_TI2_op and V_TI2_on are the output voltages V_outp and V_outn corresponding to the current inputs I_mp and I_mn, respectively.

The second sample and hold circuit 953 includes a switching element SW_SH2p, a switching element SW_SH2n, a capacitive element C_SH2p, and a capacitive element C_SH2n. The switching element SW_SH2p and the switching element SW_SH2n apply the voltages V_TI2_op and V_TI2_on to the capacitive element C_SH2p and the capacitive element C_SH2n based on a control signal φ_SH2. In response to the control signal φ_SH2 corresponding to a first level, the capacitive element C_SH2p and the capacitive element C_SH2n are charged at the voltages V_TI2_op and V_TI2_on. The second sample and hold circuit 953 outputs voltages V_SH2_op and V_SH2_on based on charges in the capacitive element C_SH2p and the capacitive element C_SH2n.

The amplifier 963 amplifies the voltages V_SH2_op and V_SH2_on to be voltages V_amp22_op and V_amp22_on, respectively. The low pass filter 973 filters the voltages V_amp22_op and V_amp22_on and outputs voltages V_LPF2_op and V_LPF2_on, respectively. Amplified values of the current inputs I_mp and I_mn are determined based on the voltages V_LPF2_op and V_LPF2_on, respectively. For example, the amplifier 963 and the low pass filter 973 are not used. In this example, the amplified value of the current inputs I_mp and I_mn are determined based on the voltages V_SH2_op and V_SH2_on, respectively.

Figure 10:
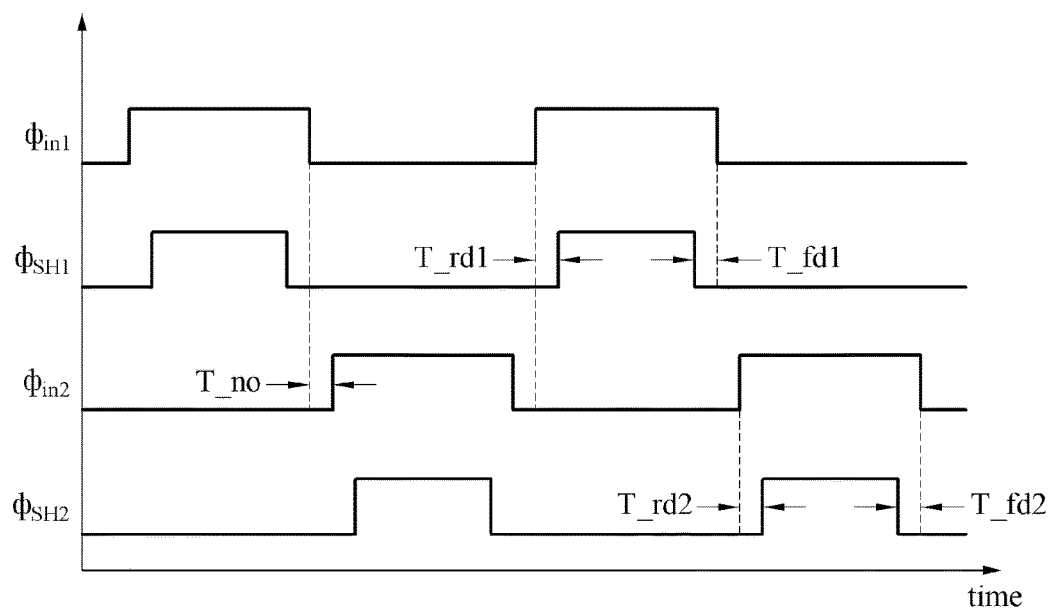
FIG. 10 illustrates an example of a control signal of an amplifier.

FIG. 10 is a timing diagram illustrating an example of a control signal of an amplifier. Referring to FIG. 10, waveforms of a control signal φ_in1, a control signal φ_SH1, a control signal φ_in2, and a control signal φ_SH2 are illustrated.

As further discussed with reference to FIG. 8, a first time interval corresponds to an interval in which a level of the control signal φ_in1 is "logical high", and a second time interval corresponds to an interval in which a level of the control signal φ_in2 is "logical high". The first time interval does not overlap the second time interval. For example, a time T_no is greater than 0. Also, a third time interval corresponds to an interval in which a level of the control signal φ_SH1 is logical high, and a fourth time interval corresponds to an interval in which a level of the control signal φ_ SH2 is logical high. The third time interval is included in the first time interval, and the fourth time interval is included in the second time interval. For example, times T_rd1, T_fd1, T_rd2, and T_fd2 are greater than 0. In an example, the first time interval of the control signal φin1 being a "logical low" is greater than the second time interval of the control signal φin2 being "logical high". The third time interval of the control signal φsh1 being a "logical high" is less than the first time interval of the control signal φin1 being "logical high". The fourth time interval of the control signal φsh2 being a "logical high" is less than the second time interval of the control signal φin2 being "logical high".

Based on the control signal φ_in1 and the control signal φ_in2, an output voltage corresponding to a voltage input is supplied to a first sample and hold circuit in the first time interval. The first sample and hold circuit generates an output signal corresponding to the voltage input in the third time interval based on the control signal φ_SH1. Also, based on the control signal φ_in1 and the control signal φ_in2, an output voltage corresponding to a current input is supplied to a second sample and hold circuit in the second time interval. The second sample and hold circuit generates an output signal corresponding to the current input in the fourth time interval based on the control signal φ_SH2. An amplified value corresponding to the voltage input is determined based on the output signal of the first sample and hold circuit, and an amplified value of the current input is restored based on the output signal of the second sample and hold circuit.

Figure 11:
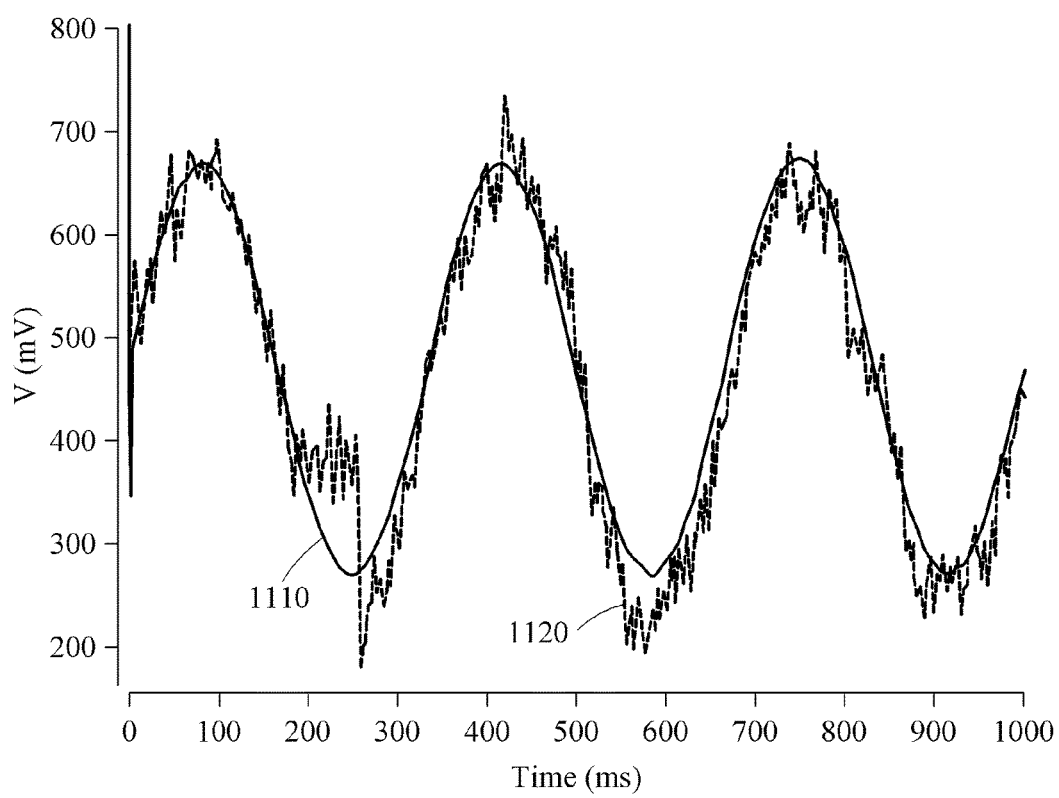
FIGS. 11 and 12 illustrate examples of a noise removal performance.
Figure 12:
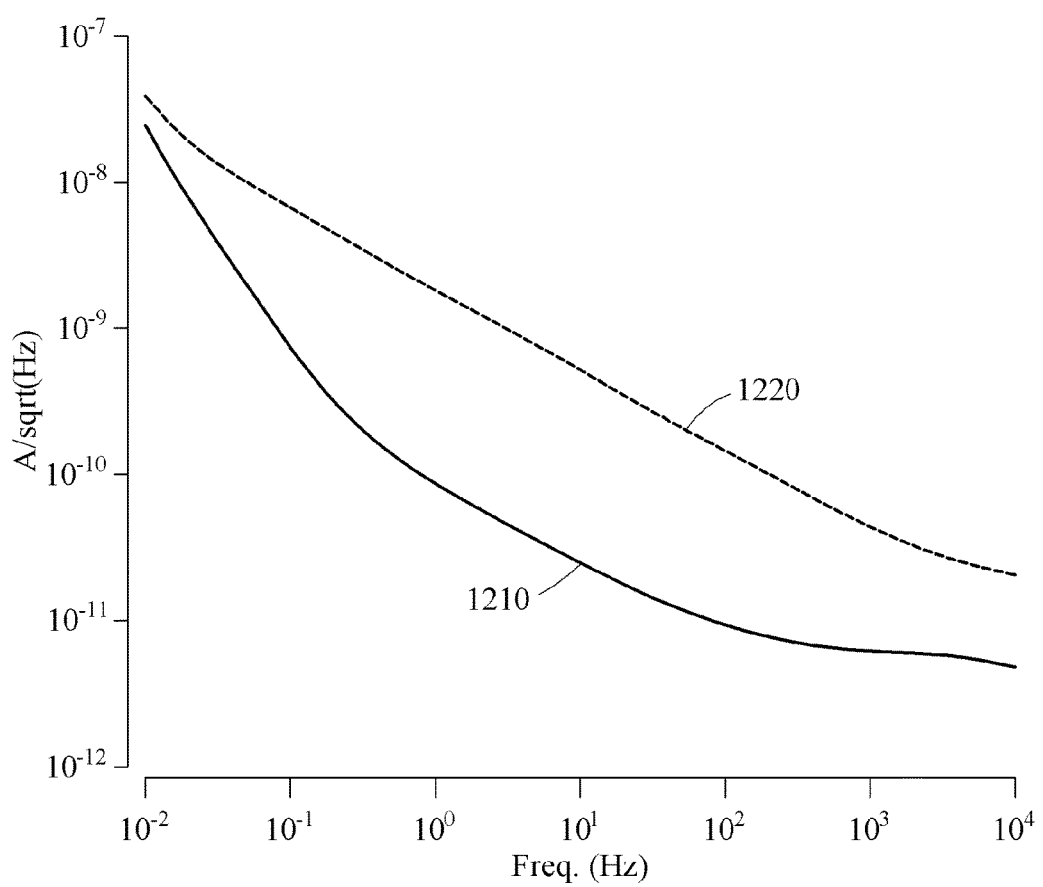

FIG. 11 and FIG. 12 are graphs illustrating examples of a noise removal performance. Referring to FIGS. 11 and 12, waveforms 1110 and 1210 correspond to an example in which a current blocker configured to block a current flowing through a load element in a first amplifying circuit is applied, and waveforms 1120 and 1220 correspond to an example in which the current blocker is not applied. As illustrated in FIGS. 11 and 12, the waveforms 1110 and 1210 include less noise in comparison to the waveforms 1120 and 1220, respectively.

Figure 13:
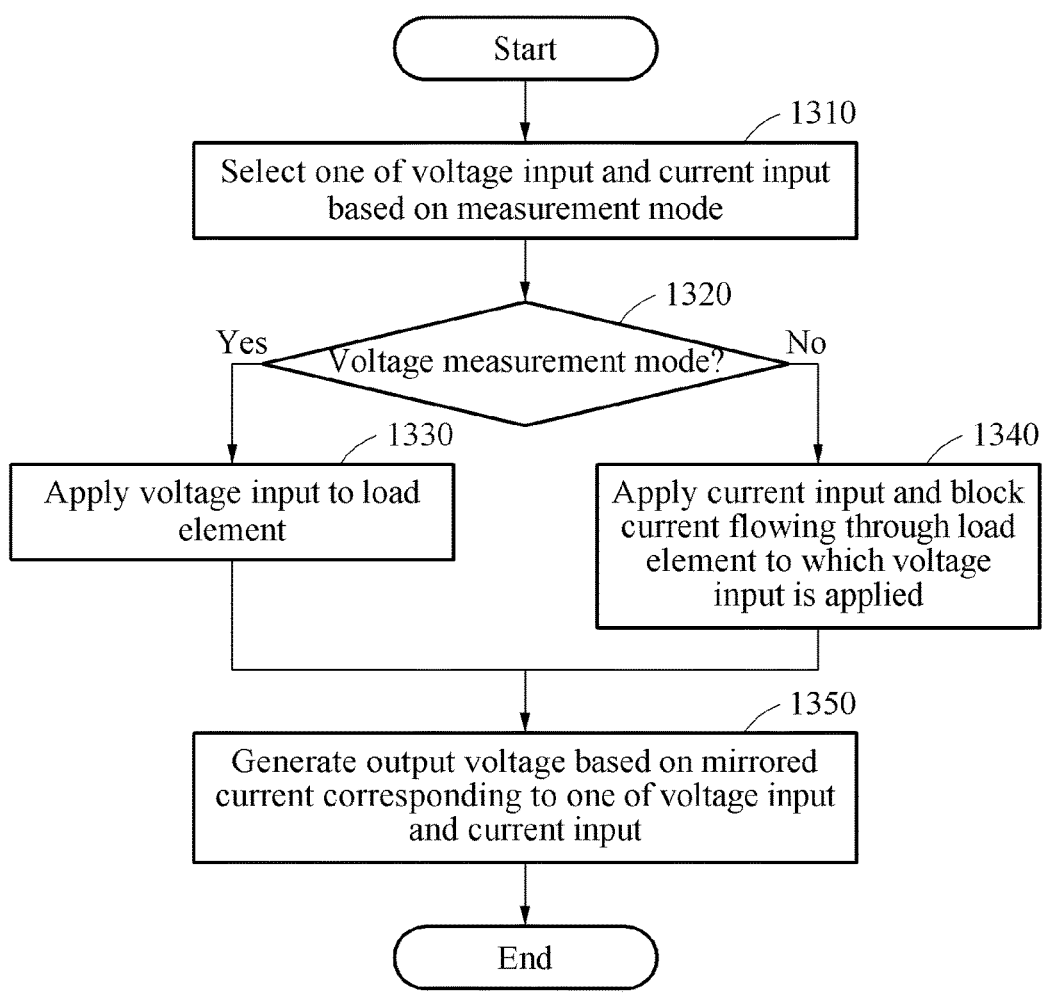
FIG. 13 illustrates an example of an amplification method.

FIG. 13 is a flowchart illustrating an example of an amplification method. Referring to FIG. 13, in operation 1310, an amplifier selects one of a voltage input and a current input based on a measurement mode. In operation 1320, the amplifier determines whether the measurement mode is a voltage measurement mode.

In response to the measurement mode being the voltage measurement mode, operation 1330 is performed. In operation 1330, the amplifier applies the voltage input to the load element.

In response to the measurement mode being a current measurement mode, operation 1340 is performed. In operation 1340, the amplifier applies a current input and blocks a current flowing through a load element to which a voltage input is applied.

After operation 1330 or operation 1340, the amplification method proceeds to operation 1350. In operation 1350, the amplifier generates an output voltage based on a mirrored current corresponding to one of the voltage input (from operation 1330) and the current input (from operation 1340). Because the foregoing description is also applicable here, repeated description about the amplification method will be omitted for brevity.

The apparatus and other apparatuses, units, selectors, elements, amplifiers, circuits, modules, devices, and other components in FIGS. 1, 2, 5, and 8 described herein are implemented by hardware components that perform the operations described in this application are implemented by hardware components configured to perform the operations described in this application that are performed by the hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The method illustrated in FIG. 13 that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations that are performed by the hardware components and the methods as described above. In one example, the instructions or software include machine code that is directly executed by the one or more processors or computers, such as machine code produced by a compiler. In another example, the instructions or software includes higher-level code that is executed by the one or more processors or computer using an interpreter. The instructions or software may be written using any programming language based on the block diagrams and the flow charts illustrated in the drawings and the corresponding descriptions in the specification, which disclose algorithms for performing the operations that are performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors or computers so that the one or more processors or computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An amplifier comprising:
   an input selector configured to select one of a voltage input and a current input based on a voltage measurement mode and a current measurement mode;
   a first amplifying circuit comprising a first load element, and configured to apply a voltage corresponding to the voltage input to the first load element in the voltage measurement mode and receive the current input in the current measurement mode and block a current flowing through the first load element, using a current blocker connected to the first load element; and
   a second amplifying circuit configured to mirror a current flowing through the first amplifying circuit in response to one of the voltage input and the current input and generate an output voltage based on the mirrored current.

2. The amplifier of claim 1, further comprising:
   the current blocker configured to be closed in the voltage measurement mode and open in the current measurement mode.

3. The amplifier of claim 1, wherein, in response to the current flowing through the first load element being blocked in the current measurement mode, noise occurring in the output voltage due to a voltage applied to the first load element is removed in the current measurement mode.

4. The amplifier of claim 1, wherein the input selector comprises:
   a voltage input selector configured to select the voltage input in the voltage measurement mode and select a preset reference voltage in the current measurement mode; and
   a current input selector configured to be open in the voltage measurement mode and select the current input in the current measurement mode.

5. The amplifier of claim 1, wherein the first amplifying circuit further comprises a transconductance element operatively connecting the input selector to the first load element.

6. The amplifier of claim 5, wherein the transconductance element is configured to generate a current corresponding to the voltage input in the voltage measurement mode, and
the voltage corresponding to the voltage input is applied to the first load element based on the generated current corresponding to the voltage input.

7. An amplifier comprising:
an input selector configured to select one of a voltage input and a current input based on a voltage measurement mode and a current measurement mode;
a first amplifying circuit comprising a first load element, and configured to apply a voltage corresponding to the voltage input to the first load element in the voltage measurement mode and receive the current input in the current measurement mode and block a current flowing through the first load element; and
a second amplifying circuit configured to mirror a current flowing through the first amplifying circuit in response to one of the voltage input and the current input and generate an output voltage based on the mirrored current, wherein the second amplifying circuit comprises a second load element to which at least a portion of the mirrored current is applied,
the output voltage is determined in the voltage measurement mode based on a mirroring ratio of the mirrored current and a ratio between a value of the first load element and a value of the second load element, and
the output voltage is determined in the current measurement mode based on the mirroring ratio of the mirrored current and the value of the second load element.

8. The amplifier of claim 1, wherein the voltage input corresponds to an electrocardiogram (ECG) signal and the current input corresponds to a photoplethysmogram (PPG) signal.

9. The amplifier of claim 1, wherein the input selector is configured to select the voltage input in a first time interval and select the current input in a second time interval, and
the first time interval does not overlap with the second time interval.

10. The amplifier of claim 9, wherein, during the first time interval of the control signal being a logical low, the second time interval of the control signal is greater than the first time interval and the second time interval is logical high.

11. The amplifier of claim 9, further comprising:
an analog-to-digital (ADC) converter configured to generate a first digital output based on the output voltage corresponding to the voltage input at a first point in time in the first time interval, and generate a second digital output based on the output voltage corresponding to the current input at a second point in time in the second time interval.

12. The amplifier of claim 9, wherein the second amplifying circuit comprises:
a first sub-amplifying circuit configured to output the output voltage based on the voltage input; and
a second sub-amplifying circuit configured to output the output voltage based on the current input.

13. The amplifier of claim 12, further comprising:
a first sample and hold circuit configured to perform a sample and hold operation on the output voltage output from the first sub-amplifying circuit in a third time interval; and
a second sample and hold circuit configured to perform a sample and operation on the output voltage output from the second sub-amplifying circuit in a fourth time interval,
wherein the third time interval is included in the first time interval and the fourth time interval is included in the second time interval.

14. An amplification method, comprising:
selecting one of a voltage input and a current input based on a measurement mode comprising a voltage measurement mode and a current measurement mode;
controlling the voltage input to be applied to a load element using a current blocker connected to the load element;
controlling the current input to be applied and a current flowing through the load element to be blocked, using the current blocker; and
generating an output voltage based on a mirrored current corresponding to one of the voltage input and the current input.

15. The amplification method of claim 14, wherein, in response to the voltage input being selected, the controlling of the voltage input comprises:
applying the voltage input to the load element; and
blocking the current input.

16. The amplification method of claim 14, wherein, in response to the current input being selected, the controlling of the current input comprises:
blocking the voltage input and the current flowing through the load element; and
receiving the current input.

17. The amplification method of claim 14, wherein, in response to the current flowing through the load element being blocked in the current measurement mode, noise occurring in the output voltage due to a voltage applied to the load element is removed.

18. The amplification method of claim 14, wherein the selecting comprises:
selecting the voltage input in a first time interval; and
selecting the current input in a second time interval, and
the first time interval does not overlap with the second time interval.

19. The amplification method of claim 18, wherein the generating of the output voltage comprises:
generating a first digital output based on the output voltage corresponding to the voltage input at a first point in time in the first time interval; and
generating a second digital output based on the output voltage corresponding to the current input at a second point in time in the second time interval.

20. The amplification method of claim 18, further comprising:
performing a sample and hold operation on the output voltage based on the voltage input in a third time interval; and
performing a sample and operation on the output voltage based on the current input in a fourth time interval,
wherein the third time interval is included in the first time interval and the fourth time interval is included in the second time interval.

21. A signal processing apparatus comprising:
a controller configured to output a control signal corresponding to one of a voltage measurement mode and a current measurement mode; and
an amplifier configured to select one of a voltage input and a current input based on the control signal, control the voltage input to be applied to a load element using a current blocker connected to the load element, control the current input to be applied and a current flowing through the load element to be blocked, and generate an output voltage based on a mirrored current corresponding to one of the voltage input and the current input.

22. An amplifier, comprising:
an input selector configured to select one of a voltage input in a voltage measurement mode, and a current input in the current measurement mode based on a control signal from a controller;
a first amplifying circuit configured to,
in the voltage measurement mode, receive the voltage input, generate a current corresponding to the voltage input, apply the voltage input a load element based on the current corresponding to the voltage input, and close a current blocker to block the current input, and
in the current measurement mode, receive the current input and open the current blocker to block a current flowing through the load element to which the voltage input is applied; and
a second amplifying circuit configured to mirror the current flowing through the first amplifying circuit based on one of the voltage input and the current input, and generate an output voltage based on the mirrored current.

23. The amplifier of claim 22, wherein the second amplifying circuit comprises a second load element, and at least a portion of the mirrored current is applied to the second load element.

24. The amplifier of claim 22, wherein, in the voltage measurement mode, the output voltage is based on a mirroring ratio of the mirrored current, and a ratio between a value of the first load element and a value of the second load element.

25. The amplifier of claim 22, wherein, in the current measurement mode, the output voltage is determined based on a mirroring ratio of the mirrored current and the value of the second load element.

26. The amplifier of claim 1, wherein the second amplifying circuit comprises a second load element to which at least a portion of the mirrored current is applied,
the output voltage is determined in the voltage measurement mode based on a mirroring ratio of the mirrored current and a ratio between a value of the first load element and a value of the second load element, and
the output voltage is determined in the current measurement mode based on the mirroring ratio of the mirrored current and the value of the second load element.

* * * * *